(12) United States Patent
Campbell

(10) Patent No.: US 11,690,709 B2
(45) Date of Patent: Jul. 4, 2023

(54) METHODS FOR SECURING A TRANSCATHETER VALVE TO A BIOPROSTHETIC CARDIAC STRUCTURE

(71) Applicant: Edwards Lifesciences Corporation, Irvine, CA (US)

(72) Inventor: Louis A. Campbell, Santa Ana, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 499 days.

(21) Appl. No.: 16/908,623

(22) Filed: Jun. 22, 2020

(65) Prior Publication Data

US 2020/0352706 A1 Nov. 12, 2020

Related U.S. Application Data

(63) Continuation of application No. 15/494,239, filed on Apr. 21, 2017, now abandoned, which is a continuation of application No. PCT/US2016/050254, filed on Sep. 2, 2016.

(60) Provisional application No. 62/213,559, filed on Sep. 2, 2015.

(51) Int. Cl.
*A61F 2/24* (2006.01)

(52) U.S. Cl.
CPC .......... *A61F 2/2409* (2013.01); *A61F 2/2418* (2013.01); *A61F 2/2448* (2013.01); *A61F 2/2412* (2013.01); *A61F 2/2433* (2013.01); *A61F 2210/0014* (2013.01); *A61F 2220/0025* (2013.01); *A61F 2230/0054* (2013.01); *A61F 2250/006* (2013.01); *A61F 2250/0063* (2013.01); *A61F 2250/0096* (2013.01)

(58) Field of Classification Search
None
See application file for complete search history.

(56) References Cited

U.S. PATENT DOCUMENTS

| 3,143,742 | A | 8/1964 | Cromie |
| 3,320,972 | A | 5/1967 | High et al. |
| 3,371,352 | A | 3/1968 | Siposs et al. |

(Continued)

FOREIGN PATENT DOCUMENTS

| EP | 0125393 A1 | 11/1984 |
| EP | 0143246 A2 | 6/1985 |

(Continued)

OTHER PUBLICATIONS

Sadowski, Jerzy; Kapelak, Boguslaw; Bartus, Krzysztof, "Sutureless Heart Valve Implantation—A Case Study," Touch Briefings, 2005, pp. 48-50. cited by other.

*Primary Examiner* — Leslie Lopez
(74) *Attorney, Agent, or Firm* — Guy Cumberbatch

(57) ABSTRACT

A spacer for creating a docking station for a transcatheter heart valve is provided. The spacer changes an effective diameter and/or a shape of an implanted bioprosthetic structure such as a bioprosthetic heart valve or annuloplasty ring, providing a supporting structure into which the transcatheter valve expands without over expanding. The spacer may be deployed through an interventional technique either through transseptal access, transfemoral access, or transapical access and is typically deployed at least in part on an inflow portion of the implanted bioprosthetic structure.

21 Claims, 7 Drawing Sheets

(56) References Cited

U.S. PATENT DOCUMENTS

| | | | |
|---|---|---|---|
| 3,409,013 A | 11/1968 | Berry | |
| 3,546,710 A | 12/1970 | Shumakov et al. | |
| 3,574,865 A | 4/1971 | Hamaker | |
| 3,628,535 A | 12/1971 | Ostrowsky et al. | |
| 3,657,744 A | 4/1972 | Ersek | |
| 3,686,740 A | 8/1972 | Shiley | |
| 3,755,823 A | 9/1973 | Hancock | |
| 3,839,741 A | 10/1974 | Haller | |
| 3,997,923 A | 12/1976 | Possis | |
| 4,035,849 A | 7/1977 | Angell et al. | |
| 4,078,468 A | 3/1978 | Civitello | |
| 4,079,468 A | 3/1978 | Liotta et al. | |
| 4,084,268 A | 4/1978 | Ionescu et al. | |
| 4,106,129 A | 8/1978 | Carpentier et al. | |
| 4,172,295 A | 10/1979 | Batten | |
| 4,217,665 A | 8/1980 | Bex et al. | |
| 4,218,782 A | 8/1980 | Rygg | |
| 4,259,753 A | 4/1981 | Liotta et al. | |
| 4,340,091 A | 7/1982 | Skelton et al. | |
| 4,343,048 A | 8/1982 | Ross et al. | |
| 4,364,126 A | 12/1982 | Rosen et al. | |
| 4,388,735 A | 6/1983 | Ionescu et al. | |
| 4,441,216 A | 4/1984 | Ionescu et al. | |
| 4,451,936 A | 6/1984 | Carpentier et al. | |
| 4,470,157 A | 9/1984 | Love | |
| 4,490,859 A | 1/1985 | Black et al. | |
| 4,501,030 A | 2/1985 | Lane | |
| 4,506,394 A | 3/1985 | Bedard | |
| 4,535,483 A | 8/1985 | Klawitter et al. | |
| 4,605,407 A | 8/1986 | Black et al. | |
| 4,626,255 A | 12/1986 | Reichart et al. | |
| 4,629,459 A | 12/1986 | Ionescu et al. | |
| 4,680,031 A | 7/1987 | Alonso | |
| 4,687,483 A | 8/1987 | Fisher et al. | |
| 4,702,250 A | 10/1987 | Ovil et al. | |
| 4,705,516 A | 11/1987 | Barone et al. | |
| 4,725,274 A | 2/1988 | Lane et al. | |
| 4,731,074 A | 3/1988 | Rousseau et al. | |
| 4,778,461 A | 10/1988 | Pietsch et al. | |
| 4,790,843 A | 12/1988 | Carpentier et al. | |
| 4,851,000 A | 7/1989 | Gupta | |
| 4,865,600 A | 9/1989 | Carpentier et al. | |
| 4,888,009 A | 12/1989 | Lederman et al. | |
| 4,914,097 A | 4/1990 | Oda et al. | |
| 4,960,424 A | 10/1990 | Grooters | |
| 4,993,428 A | 2/1991 | Arms | |
| 5,010,892 A | 4/1991 | Colvin et al. | |
| 5,032,128 A | 7/1991 | Alonso | |
| 5,037,434 A | 8/1991 | Lane | |
| 5,061,277 A * | 10/1991 | Carpentier | A61F 2/2448 623/2.36 |
| 5,147,391 A | 9/1992 | Lane | |
| 5,163,955 A | 11/1992 | Love et al. | |
| 5,258,023 A | 11/1993 | Reger | |
| 5,316,016 A | 5/1994 | Adams et al. | |
| 5,326,370 A | 7/1994 | Love et al. | |
| 5,326,371 A | 7/1994 | Love et al. | |
| 5,332,402 A | 7/1994 | Teitelbaum | |
| 5,360,444 A | 11/1994 | Kusuhara | |
| 5,370,685 A | 12/1994 | Stevens | |
| 5,376,112 A | 12/1994 | Duran | |
| 5,396,887 A | 3/1995 | Imran | |
| 5,397,351 A | 3/1995 | Pavcnik et al. | |
| 5,411,522 A | 5/1995 | Trott | |
| 5,423,887 A | 6/1995 | Love et al. | |
| 5,425,741 A | 6/1995 | Lemp et al. | |
| 5,431,676 A | 7/1995 | Dubrul et al. | |
| 5,449,384 A | 9/1995 | Johnson | |
| 5,449,385 A | 9/1995 | Religa et al. | |
| 5,469,868 A | 11/1995 | Reger | |
| 5,476,510 A | 12/1995 | Eberhardt et al. | |
| 5,488,789 A | 2/1996 | Religa et al. | |
| 5,489,297 A | 2/1996 | Duran | |
| 5,489,298 A | 2/1996 | Love et al. | |
| 5,500,016 A | 3/1996 | Fisher | |
| 5,533,515 A | 7/1996 | Coller et al. | |
| 5,549,665 A | 8/1996 | Vesely et al. | |
| 5,562,729 A | 10/1996 | Purdy et al. | |
| 5,571,215 A | 11/1996 | Sterman et al. | |
| 5,573,007 A | 11/1996 | Bobo, Sr. | |
| 5,578,076 A | 11/1996 | Krueger et al. | |
| 5,584,803 A | 12/1996 | Stevens et al. | |
| 5,618,307 A | 4/1997 | Donlon et al. | |
| 5,626,607 A | 5/1997 | Malecki et al. | |
| 5,628,789 A | 5/1997 | Vanney et al. | |
| 5,693,090 A | 12/1997 | Unsworth et al. | |
| 5,695,503 A | 12/1997 | Krueger et al. | |
| 5,713,952 A | 2/1998 | Vanney et al. | |
| 5,716,370 A | 2/1998 | Williamson, IV et al. | |
| 5,728,064 A | 3/1998 | Burns et al. | |
| 5,728,151 A | 3/1998 | Garrison et al. | |
| 5,735,894 A | 4/1998 | Krueger et al. | |
| 5,752,522 A | 5/1998 | Murphy | |
| 5,755,782 A | 5/1998 | Love et al. | |
| 5,766,240 A | 6/1998 | Johnson | |
| 5,776,187 A | 7/1998 | Krueger et al. | |
| 5,776,188 A | 7/1998 | Shepherd et al. | |
| 5,800,527 A | 9/1998 | Jansen et al. | |
| 5,814,097 A | 9/1998 | Sterman et al. | |
| 5,814,098 A | 9/1998 | Hinnenkamp et al. | |
| 5,824,064 A | 10/1998 | Taheri | |
| 5,824,068 A | 10/1998 | Bugge | |
| 5,840,081 A | 11/1998 | Andersen et al. | |
| 5,848,969 A | 12/1998 | Panescu et al. | |
| 5,855,563 A | 1/1999 | Kaplan et al. | |
| 5,855,601 A | 1/1999 | Bessler et al. | |
| 5,865,801 A | 2/1999 | Houser | |
| 5,891,160 A | 4/1999 | Williamson, IV et al. | |
| 5,895,420 A | 4/1999 | Mirsch, II et al. | |
| 5,902,308 A | 5/1999 | Murphy | |
| 5,908,450 A | 6/1999 | Gross et al. | |
| 5,919,147 A | 7/1999 | Jain | |
| 5,921,934 A | 7/1999 | Teo | |
| 5,921,935 A | 7/1999 | Hickey | |
| 5,924,984 A | 7/1999 | Rao | |
| 5,928,281 A | 7/1999 | Huynh et al. | |
| 5,957,949 A | 9/1999 | Leonhardt et al. | |
| 5,972,004 A | 10/1999 | Williamson, IV et al. | |
| 5,984,959 A | 11/1999 | Robertson et al. | |
| 5,984,973 A | 11/1999 | Girard et al. | |
| 6,010,531 A | 1/2000 | Donlon et al. | |
| 6,042,607 A | 3/2000 | Williamson, IV et al. | |
| 6,053,873 A | 4/2000 | Govari et al. | |
| 6,059,827 A | 5/2000 | Fenton, Jr. | |
| 6,066,160 A | 5/2000 | Colvin et al. | |
| 6,074,418 A | 6/2000 | Buchanan et al. | |
| 6,081,737 A | 6/2000 | Shah | |
| 6,083,179 A | 7/2000 | Oredsson | |
| 6,099,475 A | 8/2000 | Seward et al. | |
| 6,106,550 A | 8/2000 | Magovern et al. | |
| 6,110,200 A | 8/2000 | Hinnenkamp | |
| 6,117,091 A | 9/2000 | Young et al. | |
| 6,126,007 A | 10/2000 | Kari et al. | |
| 6,264,611 B1 | 7/2001 | Ishikawa et al. | |
| 6,322,526 B1 | 11/2001 | Rosenman et al. | |
| 6,350,282 B1 | 2/2002 | Eberhardt | |
| 6,491,624 B1 | 12/2002 | Lotfi | |
| 6,773,457 B2 | 8/2004 | Ivancev et al. | |
| 7,037,333 B2 | 5/2006 | Myers et al. | |
| 7,998,151 B2 | 8/2011 | St. Goar et al. | |
| 8,308,798 B2 | 11/2012 | Pintor et al. | |
| 8,323,337 B2 | 12/2012 | Gurskis et al. | |
| 8,348,998 B2 | 1/2013 | Pintor et al. | |
| 9,072,604 B1 | 7/2015 | Melnick et al. | |
| 2001/0021872 A1 | 9/2001 | Bailey et al. | |
| 2001/0039435 A1 | 11/2001 | Roue et al. | |
| 2001/0039436 A1 | 11/2001 | Frazier et al. | |
| 2001/0041914 A1 | 11/2001 | Frazier et al. | |
| 2001/0041915 A1 | 11/2001 | Roue et al. | |
| 2001/0049492 A1 | 12/2001 | Frazier et al. | |
| 2002/0026238 A1 | 2/2002 | Lane et al. | |
| 2002/0032481 A1 | 3/2002 | Gabbay | |
| 2002/0058995 A1 | 5/2002 | Stevens | |
| 2002/0123802 A1 | 9/2002 | Snyders | |

(56) References Cited

U.S. PATENT DOCUMENTS

| | | |
|---|---|---|
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210305 A1 | 10/2004 | Shu et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0137702 A1 | 6/2005 | Haug et al. |
| 2005/0159811 A1 | 7/2005 | Lane |
| 2005/0165477 A1 | 7/2005 | Anduiza et al. |
| 2005/0165479 A1 | 7/2005 | Drews et al. |
| 2005/0182483 A1 | 8/2005 | Osborne et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240259 A1 | 10/2005 | Sisken et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0122692 A1 | 6/2006 | Gilad et al. |
| 2006/0136054 A1 | 6/2006 | Berg et al. |
| 2006/0149360 A1 | 7/2006 | Schwammenthal et al. |
| 2006/0154230 A1 | 7/2006 | Cunanan et al. |
| 2006/0161249 A1 | 7/2006 | Realyvasquez et al. |
| 2006/0167543 A1 | 7/2006 | Bailey et al. |
| 2006/0195183 A1 | 8/2006 | Navia et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0229708 A1 | 10/2006 | Powell et al. |
| 2006/0235508 A1 | 10/2006 | Lane et al. |
| 2006/0241745 A1 | 10/2006 | Solem |
| 2006/0246888 A1 | 11/2006 | Bender et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2006/0293745 A1 | 12/2006 | Carpentier et al. |
| 2007/0005129 A1 | 1/2007 | Damm et al. |
| 2007/0010876 A1 | 1/2007 | Salahieh et al. |
| 2007/0010877 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244546 A1 | 10/2007 | Francis |
| 2007/0244558 A1 | 10/2007 | Machiraju |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0021546 A1 | 1/2008 | Patz et al. |
| 2008/0033527 A1* | 2/2008 | Nunez ............... A61F 2/07 623/1.13 |
| 2008/0033543 A1 | 2/2008 | Gurskis et al. |
| 2008/0065198 A1 | 3/2008 | Quintessenza |

(56) References Cited

U.S. PATENT DOCUMENTS

| | | |
|---|---|---|
| 2008/0119875 A1 | 5/2008 | Ino et al. |
| 2008/0154356 A1 | 6/2008 | Obermiller et al. |
| 2008/0208327 A1* | 8/2008 | Rowe .................. A61F 2/2427 604/509 |
| 2008/0215144 A1 | 9/2008 | Ryan et al. |
| 2008/0281411 A1 | 11/2008 | Berreklouw |
| 2008/0319543 A1 | 12/2008 | Lane |
| 2009/0036903 A1 | 2/2009 | Ino et al. |
| 2009/0192599 A1 | 7/2009 | Lane et al. |
| 2009/0192602 A1 | 7/2009 | Kuehn |
| 2009/0192603 A1 | 7/2009 | Kuehn |
| 2009/0192604 A1 | 7/2009 | Gloss |
| 2009/0192605 A1 | 7/2009 | Gloss et al. |
| 2009/0192606 A1 | 7/2009 | Gloss et al. |
| 2010/0161036 A1 | 6/2010 | Pintor et al. |
| 2010/0168836 A1* | 7/2010 | Kassab ................ A61F 2/2433 623/1.11 |
| 2010/0249894 A1 | 9/2010 | Oba et al. |
| 2010/0249908 A1 | 9/2010 | Chau et al. |
| 2010/0331972 A1 | 12/2010 | Pintor et al. |
| 2011/0022165 A1 | 1/2011 | Oba et al. |
| 2011/0040372 A1 | 2/2011 | Hansen et al. |
| 2011/0147251 A1 | 6/2011 | Hodshon et al. |
| 2011/0166636 A1 | 7/2011 | Rowe |
| 2012/0065729 A1 | 3/2012 | Pintor et al. |
| 2012/0141656 A1 | 6/2012 | Orr et al. |
| 2012/0150288 A1 | 6/2012 | Hodshon et al. |
| 2012/0283820 A1 | 11/2012 | Tseng et al. |
| 2013/0053949 A1 | 2/2013 | Pintor et al. |
| 2013/0116777 A1 | 5/2013 | Pintor et al. |
| 2014/0058194 A1 | 2/2014 | Soletti et al. |
| 2014/0079758 A1 | 3/2014 | Hall et al. |
| 2014/0188221 A1* | 7/2014 | Chung ................ A61F 2/2409 623/2.18 |
| 2014/0257466 A1 | 9/2014 | Board et al. |
| 2015/0190227 A1 | 7/2015 | Johnson et al. |

FOREIGN PATENT DOCUMENTS

| | | |
|---|---|---|
| WO | 9213502 A1 | 8/1992 |
| WO | 9742871 A1 | 11/1997 |
| WO | 2007146261 A2 | 12/2007 |

* cited by examiner

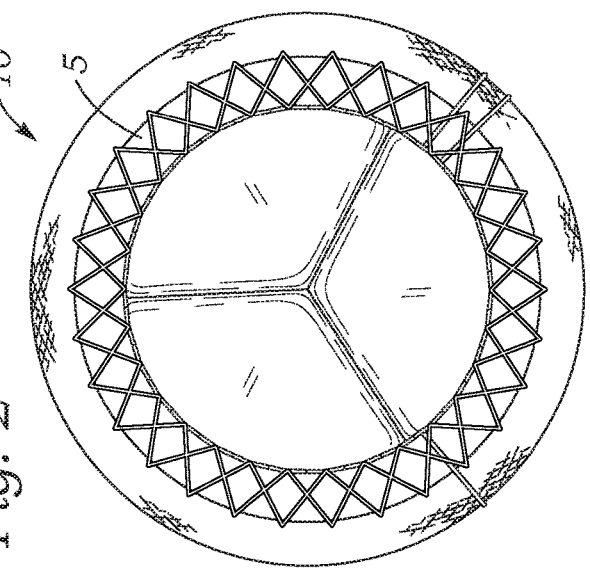
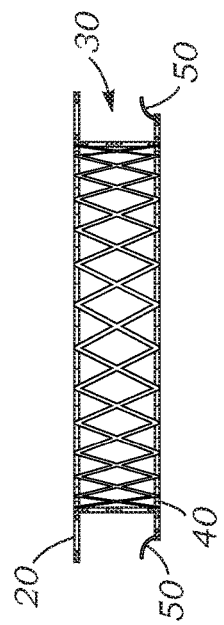
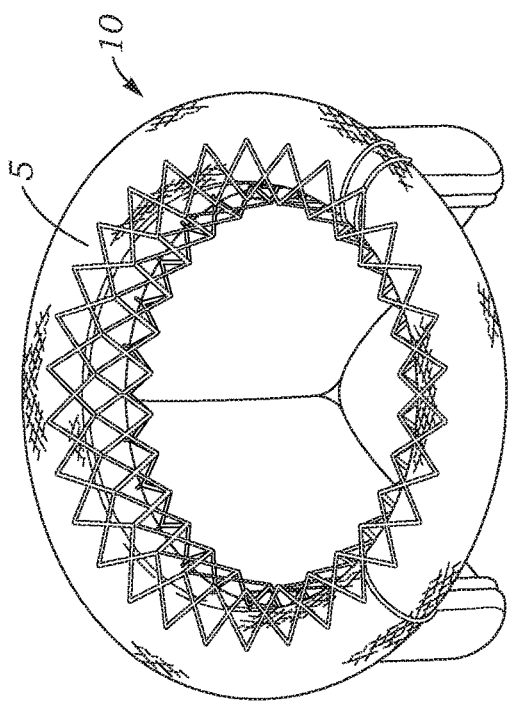
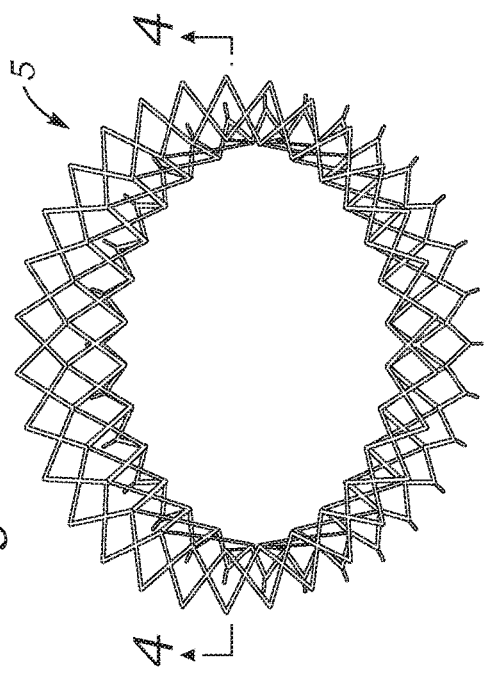

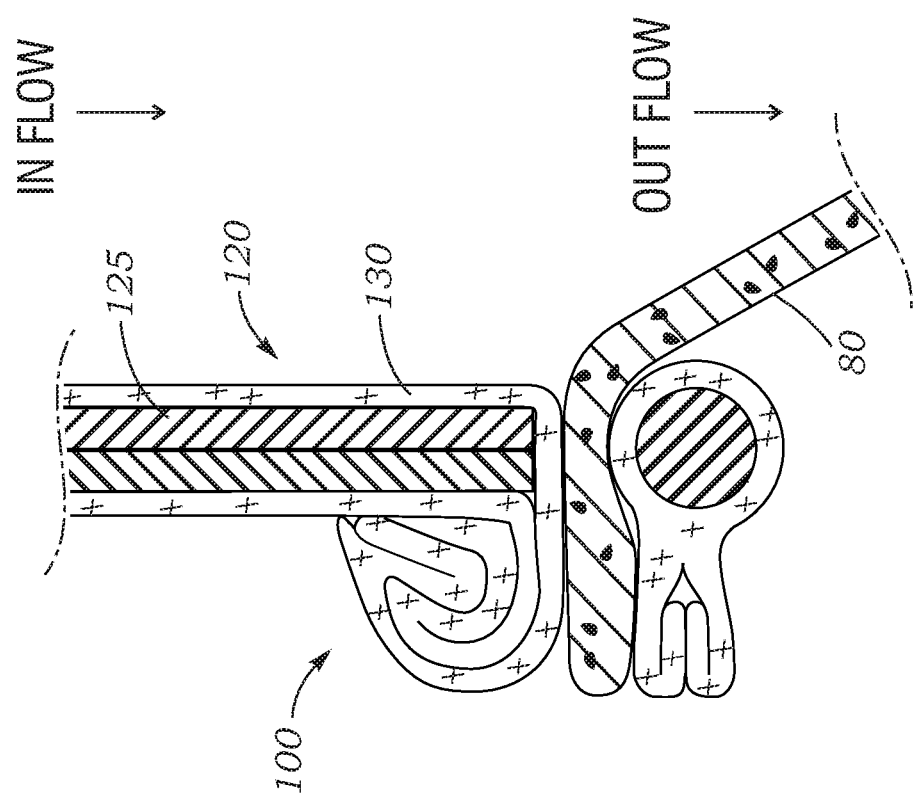

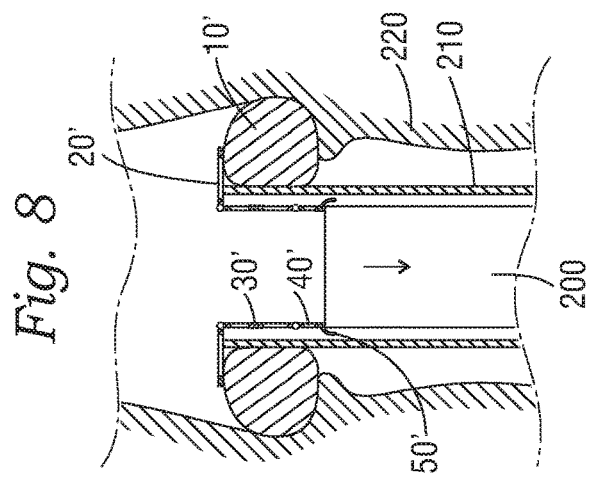
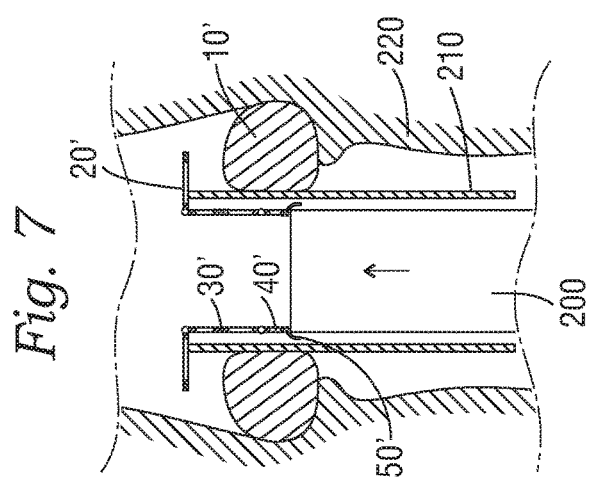
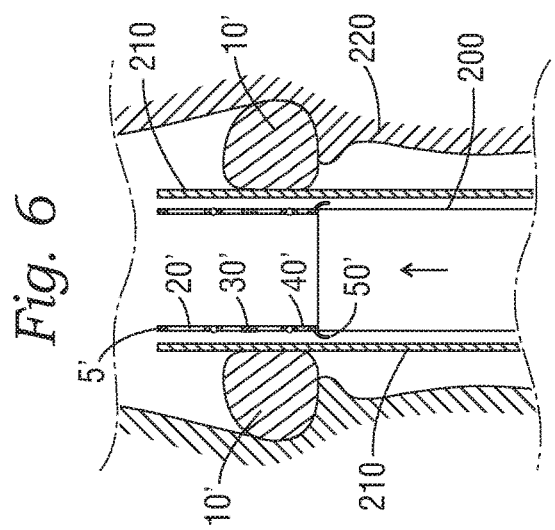
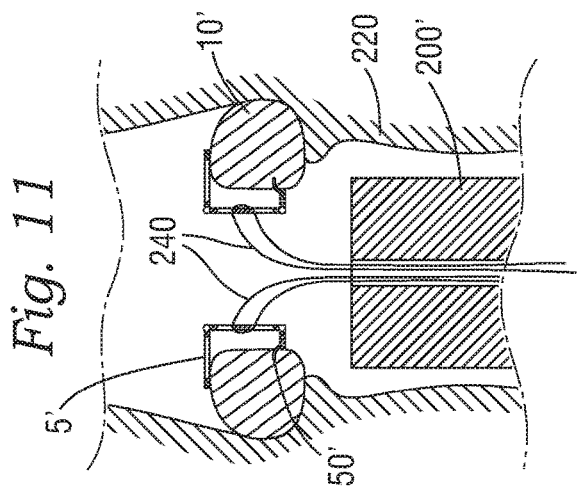
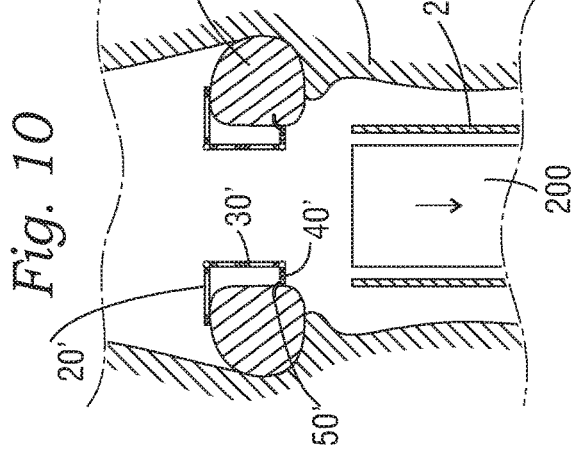
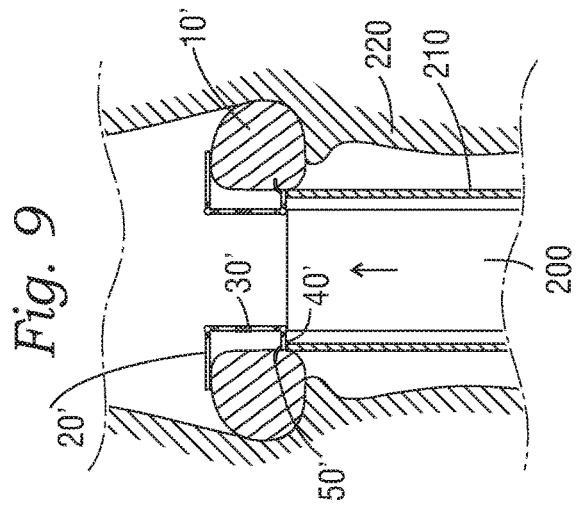

METHODS FOR SECURING A TRANSCATHETER VALVE TO A BIOPROSTHETIC CARDIAC STRUCTURE

CROSS REFERENCE TO RELATED APPLICATIONS

This application is a continuation of U.S. patent application Ser. No. 15/494,239, filed Apr. 21, 2017, which is a continuation of International Patent Application No. PCT/US2016/050254, filed Sep. 2, 2016, which claims the benefit of U.S. Patent Application No. 62/213,559, filed Sep. 2, 2015, the entire disclosures of which are incorporated by reference herein.

TECHNICAL FIELD

The present disclosure relates to transcatheter valve implantation in a bioprosthetic valve or a native valve that has been repaired with an annuloplasty ring and, in particular, an apparatus and method to assist in securing the transcatheter valve in the bioprosthetic valve or to the annuloplasty ring.

BACKGROUND

Valve-in-valve transcatheter valve implantation is increasingly used when bioprosthetic heart valves fail. Bioprosthetic valves are used more often than mechanical valves, and increasingly, in younger patients. Although the durability of bioprosthetic valves has improved, some patients outlive the life of the valve, for example, when structural deterioration causes the valve to fail. For a younger person with a bioprosthetic valve replacement, there is a significant likelihood that another valve replacement will be needed later in life. In such a replacement, the new valve may be a transcatheter valve (THV) that is placed within the existing bioprosthetic valve without the need for open-heart surgery.

There are transcatheter valves that are appropriately sized to be placed inside most aortic bioprosthetic valves. Such transcatheter valves are too small to be secured into some larger bioprosthetic valve sizes, however. A challenge with valve-in-valve replacements in the larger valves is that the transcatheter valve may not be large enough to sufficiently expand inside the implanted tissue valve to stay in place and to be competent. If the transcatheter valve is expanded too much, the leaflets of the valve may not properly come together or coapt for the valve to function properly.

Similarly, it may be necessary to implant a transcatheter valve in a native valve that has been repaired with an annuloplasty band. Annuloplasty is a technique for repairing valves. An annuloplasty ring is implanted surrounding the valve annulus, pulling the leaflets together to facilitate coaptation and proper function of the native valve leaflets. The annuloplasty ring may have a non-circular configuration, such as a D-shape as just one example, particularly when the ring is used in conjunction with the mitral valve. A spacer according to the present invention may be adapted to secure to a suitable annuloplasty ring, in order to provide a structure into which a transcatheter heart valve may be expanded and secured.

BRIEF SUMMARY

In one embodiment a spacer, which may alternatively be referred to as a THV docking station herein, is provided for implantation into a bioprosthetic cardiac structure such as bioprosthetic heart valve or an annuloplasty ring that has a central flow axis, an upstream direction and a downstream direction. The downstream direction corresponds to the direction of blood flow from an upstream portion of the bioprosthetic structure, and through flaps in a downstream portion of a heart valve when the spacer is implanted. The spacer has a transcatheter valve mounting surface.

Considering optional features that may additionally be used, either alone or in combination with one another, the spacer may include a first flange for mounting on an upstream surface of the bioprosthetic structure and a spacer shaft. The spacer may optionally also have a second flange for mounting on the bioprosthetic structure in the downstream direction relative to the first flange. In an embodiment in which the spacer has both a first and a second flange, the spacer shaft interconnects the first flange and the second flange. As a further alternative, the spacer may have a spacer shaft secured to an interior surface of the existing bioprosthetic structure, without a first or second flange.

The first flange may optionally have a dimension that is greater than that of the second flange and of an inner diameter of the bioprosthetic structure. The second flange may optionally be adapted to be secured to an inner diameter of a cylindrical space in an upstream portion of the bioprosthetic structure relative to valve leaflets that are in a downstream direction relative to the cylindrical space. The spacer may optionally include spikes or other attachment means known in the art for securing the spacer to the bioprosthetic heart valve. In one embodiment, the second flange includes such spikes.

In one aspect, the spacer includes a shape memory material and is self-expanding for transcatheter delivery into the bioprosthetic valve. Alternatively, at least a portion of the spacer may be balloon-expandable.

Considering other optional features, the spacer may include snares connected thereto to control expansion of the spacer ring during deployment. At least a portion of the spacer may be covered with fabric or other blood-impermeable material. The spacer may comprise, for example, a cobalt-chromium alloy, nitinol, stainless steel, and/or other materials known in the art. The second flange may be adapted to secure to a stiffening band in a cylindrical space in an upstream portion of the bioprosthetic structure. The first and/or second flanges may optionally be rings. The spacer shaft may optionally be substantially cylindrical. In one embodiment, the spacer includes sensors that communicate sensor data. The shaft into which a THV may dock may be spring loaded. The shaft into which a THV may dock comprises a compressible surface.

Another aspect is a method of providing a securing surface for a transcatheter valve within a bioprosthetic structure. The structure has a central flow axis with an upstream direction and a downstream direction, the downstream direction corresponding to the direction of blood flow from an upstream portion of the bioprosthetic structure through flaps in a downstream portion of the structure when a spacer is implanted. The method may include providing a collapsible spacer for a bioprosthetic structure, collapsing the spacer to a reduced diameter, coupling the spacer to a distal end portion of an elongate catheter, advancing the elongate catheter through a patient's vasculature and delivering the spacer into position relative to the bioprosthetic structure, and expanding the spacer to provide an engagement surface for a transcatheter heart valve.

Considering further optional features of the method that may additionally be used, either alone or in combination with one another, the method may further include expanding an upstream spacer flange such that an outside dimension of the upstream spacer flange is greater than the inside diameter of an upstream end of the bioprosthetic structure. The upstream spacer flange may be positioned into contact with an upstream end surface of the bioprosthetic structure, and then expansion of the spacer completed. The spacer may, for example, be secured within the bioprosthetic structure, the downstream portion of the spacer being positioned upstream of flaps of the bioprosthetic heart valve or the native heart valve.

After being fixed within the bioprosthetic structure, the spacer ring may have an upstream flange mounted on an upstream surface of the bioprosthetic structure, and a spacer engagement surface extending downstream and toward valve flaps. The method may also include expanding a transcatheter heart valve within the bioprosthetic structure, the transcatheter heart valve securing to a surface of the spacer. The spacer may be sequentially pushed out of a delivery system, an upstream flange being first pushed out of the delivery system and flipping into position, the upstream flange pulled to the valve, and the remainder of the spacer pushed out to complete expansion of the spacer.

As the spacer is expanded, spikes on the spacer may be secured into the implanted bioprosthetic structure to maintain the spacer in position. As one example, the spikes may be secured into an inner diameter of the bioprosthetic structure. In one embodiment, the inner diameter of the bioprosthetic structure is covered with cloth, fabric, or other covering, and the spikes are secured into the covering. In another aspect, the spacer may have a downstream flange, with spikes extending from the downstream flange, and the step of the spikes securing into the inner diameter of the bioprosthetic structure may include securing spikes that extend from the downstream flange into the inner diameter of the bioprosthetic structure upstream of flaps of the valve.

Expansion of the spacer may be accomplished with a spacer that is self-expandable. Alternatively, the step of expanding the spacer may be at least partially accomplished with a balloon. In a further optional feature, the method may include a step of controlling expansion of the spacer with snares that are coupled to the spacer.

In one embodiment, the spacer has an upstream ring flange and the method comprises the step of engaging the upstream ring flange with an upstream portion of the bioprosthetic structure. The spacer may include a downstream ring flange, and the method includes the step of engaging the downstream ring flange with a downstream portion of the bioprosthetic structure.

Again, the disclosed concept includes variations, and the optional features noted above may be added to embodiments of the invention, either alone or in various combinations as appropriate.

A further understanding of the nature and advantages will become apparent by reference to the remaining portions of the specification and drawings.

BRIEF DESCRIPTION OF THE DRAWINGS

FIG. 1 illustrates an embodiment of a spacer mounted onto a bioprosthetic mitral, tricuspid or aortic valve;

FIG. 2 is a top view of the spacer of FIG. 1;

FIG. 3 is a perspective view of the spacer of FIGS. 1 and 2;

FIG. 4 is a cross-section of the spacer ring of FIG. 3;

FIG. 5 is a cross-section of one embodiment of a surgical bioprosthetic valve illustrating a stiffening ring and a covering;

FIG. 6 is a cross-sectional view of a catheter delivery system with one non-limiting example of a self-expanding spacer ring inside, ready for deployment onto the bioprosthetic valve;

FIG. 7 illustrates a catheter delivery system of FIG. 6, with a pusher pushing a self-expanding upper ring flange portion of the spacer out of the delivery system;

FIG. 8 illustrates the expanded upper ring flange portion pulled into place on an upstream portion of the bioprosthetic valve;

FIG. 9 is the system of FIG. 8, with the spacer wall and the lower ring flange expanded into position and the spikes on the lower ring flange securing the spacer into fabric within the bioprosthetic valve;

FIG. 10 illustrates the delivery system being pulled away after the spacer ring has been implanted;

FIG. 11 illustrates an alternative embodiment in which snares control expansion of the spacer;

DETAILED DESCRIPTION

Figure 13:
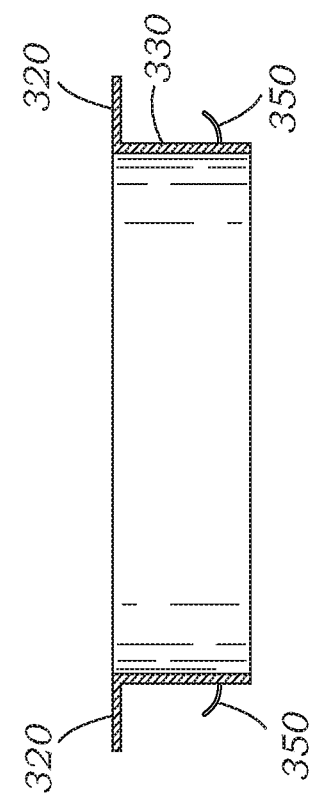
FIG. 13 illustrates the spacer ring of FIG. 12 in cross-section.

FIG. 1 illustrates one embodiment of a spacer ring 5 deployed in a surgical mitral or tricuspid prosthetic valve 10, for example, a Carpentier-Edwards PERIMOUNT Magna Mitral Ease® mitral heart valve (Model 7300TFX, Edwards Lifesciences, Irvine, Calif.). The spacer ring 5 is provided to narrow or reduce the space within an implanted bioprosthetic mitral, tricuspid, pulmonic, or aortic valve 10 into which the transcatheter valve is to be implanted, for example, a surgically implantable bioprosthetic valve. As discussed above, the spacer ring 5 is useful in situations in which an interior space or lumen of a previously implanted prosthetic valve is too large for direct implantation of a largest available transcatheter valve therein. FIG. 2 is a top view of the same spacer ring 5 in place on the surgical mitral or tricuspid valve 10. FIG. 3 is a perspective view of the spacer ring itself, and FIG. 4 is a cross-section of the spacer ring of FIG. 3.

Considering FIG. 4, the spacer has a first ring flange 20 on the upstream side, a spacer shaft 30 with an interior surface to which a transcatheter heart valve may secure, and a downstream lower ring flange 40 having anchors, barbs, or spikes 50. The spikes 50 are provided to secure the spacer ring to fabric on the interior of the surgical bioprosthetic valve. It is noted that the terms "upstream" and "downstream" are used in conjunction with an embodiment in which a bioprosthetic valve is the bioprosthetic structure to which the spacer is to attach, for example, and that the terms as used with other bioprosthetic structures to which the spacer attaches may simply refer to relative positions rather than strictly to directions in which blood flows.

FIGS. 1 and 2 illustrate a spacer 10 secured in place on bioprosthetic surgical heart valve 10. Once the spacer is in place, a transcatheter valve can be placed in the bioprosthetic valve in the same fashion as would be done in a smaller surgical valve, in which a spacer ring is not needed, with the transcatheter valve engaging the interior surface on the spacer that has been placed in the bioprosthetic valve. The spacer provides axial support for the transcatheter valve, so that the transcatheter valve will not move in either the upstream or the downstream direction, as well as radial support for an outer wall or stent of the transcatheter valve, thereby reducing a risk of over-expanding the transcatheter valve.

FIG. 5 is a cross-sectional view of a representative surgical bioprosthetic aortic valve 100, such as the Carpentier-Edwards PERIMOUNT® aortic heart valve (Model 2700TFX, Edwards Lifesciences) as just one example. The spacer and method are also adaptable to other prosthetic valves, for example, prosthetic valves with other structural details, as well as prosthetic valves designed for other native valve locations including pulmonic, mitral, and tricuspid prosthetic valves, as discussed above. As seen, the valve 100 has an inflow direction corresponding to the direction blood flows into the valve. The valve also has an outflow direction corresponding to the direction the blood flows as it exits the valve through the flaps (leaflets). The valve includes a fabric-covered stent portion supporting valve leaflets 80. On the inflow side of the valve is an annular cuff. On the interior of the valve is a generally cylindrical space 120, illustrated in the cross-sectional view of FIG. 5, backed by a stiffening ring 125 in the illustrated embodiment. Other embodiments of the valve do not include a stiffening ring. The interior is covered with fabric or other covering known in the art 130. This provides a space 120 onto which the spacer 10 (FIGS. 1-4) may mount on the inflow portion of the valve without substantially interfering with the operation of the leaflets 80, which could make the tissue valve incompetent. The spacer may be deployed through an interventional technique, for example, either through transseptal access, transfemoral access, or transapical access, and is typically deployed on or near the inflow end of the implanted bioprosthetic valve. Alternatively, the spacer may be deployed surgically, for example, in a minimally-invasive surgical (MIS) procedure.

Positioning a device within a beating heart can be difficult, for example, including one or more challenging steps. FIG. 6 is a cross-sectional view of a catheter 210 inserted within an artery 220 for delivery of the spacer 5'. The spacer 5' includes upstream flange portion 20', spacer surface portion 30', and downstream flange portion 40' having spikes 50'. A pusher 200 pushes the spacer 5' upstream for delivery onto existing bioprosthetic valve 10'. In one embodiment the spacer is partially expanded such that the outside diameter of the upstream flange of the spacer is larger than the inside diameter of the surgical valve, as seen in FIG. 7. The spacer can then be pulled from the atrial position illustrated in FIG. 7 into contact with the implanted bioprosthetic valve (FIG. 8), where the expansion would be completed (FIG. 9), for example, by retracting the catheter 210 and/or adjusting a position of the pusher 200.

In FIG. 10, the delivery system including the catheter 210 and the pusher 200' is pulled away from the spacer 5' and bioprosthetic valve 10'. This approach permits aligning the spacer on the inflow aspect of the implanted valve without causing the surgical valve to become incompetent. With this approach, the spacer may be either a balloon-expandable device or a controlled self-expanding device. As seen in FIGS. 1 and 2, the structure of the spacer ring includes a series of struts, most commonly defining diamond-shaped cells, but in the alternative includes chevron-shaped cells, rectangular cells, and/or other cell shapes known in the art, and combinations thereof. The spacer may be expanded by other balloon and/or mechanical expansion methods known in the art. The spacer may also be partially self-expanding and partially balloon-expanded. As just one example, the upstream and/or downstream flanges may self-expanding, for example, while the central portion of the spacer is balloon-expanded. Entirely self-expanding embodiments can also be balloon expanded post-initial deployment, for example, to ensure that the spacer is fully expanded and/or to seat any anchors.

Considering this process in more detail, FIG. 6 illustrates a self-expanding spacer assembly 5' inside a transcatheter delivery system in cross-section. In the illustrated embodiment, the spacer 5' is in a delivery configuration in the catheter 210, with the upstream flange 20', spacer shaft 30', and downstream flange 40' each extending generally longitudinally, and with the upstream flange 20' and downstream flange 40' radially compressed. In some embodiments, the spacer shaft 30' is also radially compressed. The illustrated embodiment also includes a plurality of optional engagement means, engagement elements, or anchors 50', which in other embodiments have a different configuration. As a pusher 200 pushes the spacer assembly 5' out of the catheter 210, the upstream flange 20' first extends longitudinally out of the opening at the distal end of the catheter 210, then flips or rotates down into a generally horizontal or radial position, as seen in FIGS. 6 and 7. The spacer and catheter are then pulled or retracted proximally so that the spacer contacts the valve, and expansion of the spacer, including spacer shaft 30' and downstream ring 40', continues as the spacer 5' is urged out of the catheter 210, for example, by retracting the catheter while preventing proximal movement of the spacer 5' using the pusher 200, as shown in FIG. 8. A series of spikes 50' on the downstream ring 40' then flip from a longitudinal delivery configuration to a radial deployed configuration as the downstream ring 40' does the same. In the embodiment illustrated in FIG. 9, the pusher 200 is urged distally, for example, urging the downstream ring 40' into the final deployed configuration and/or urging the anchors or spikes 50' into the fabric disposed around the inner diameter of the implanted bioprosthetic valve 10' to maintain and to secure the spacer in position. As the spacer is pushed out of the delivery system, the spikes 50' extend across the inner diameter and into fabric of the surgical valve. As an alternative, the flanges 20' and 40' may be deployed to sandwich the structure 10' to hold the spacer in place.

In a preferred embodiment, the upstream and downstream flanges and the spacer shaft are, in plan view, ring-shaped. However, it is noted that the flanges and the spacer shaft may take forms other than rings. Further, the upstream and downstream flanges and the spacer shaft may have different plan, cross-sectional geometries from one another, so long as they serve their respective purposes in the spacer assembly.

FIG. 11 illustrates that in an alternative embodiment, expansion of the spacer after leaving the delivery system may be controlled by snares 240. The snares 240 may be loops of suture material or wire, for example, or another suitable design. In one approach, the snares 240 extend up through a passageway in a pusher 200'. Expansion of the spacer 5' is then controlled when the snares 240 are held relatively tightly in tension, then the tension released in a controlled manner, for example, gradually, until the spacer 5' is in position, or in any manner appropriate in a given situation.

In some bioprosthetic valves, for example, certain bioprosthetic valves manufactured and provided by Edwards Lifesciences, the valve has a stiffening ring 125, as illustrated in FIG. 5. The stiffening ring 125 is typically a fabric-covered or otherwise covered ring preferably made of cobalt-chromium alloy (e.g., ELGILOY® alloy, Elgiloy Specialty Metals, Elgin, Ill.) that extends around the inflow aspect of the prosthetic valve, although the stiffening ring may include other materials, for example, any combination of stainless steel, nitinol, cobalt-chromium, and polymer. The stiffening ring 125 stabilizes and strengthens the prosthetic valve. As seen in FIG. 10, for example, length of the spacer portion and the lower ring is sufficiently short so as to ensure that the spiked portion of the spacer rings does not extend into or contact the leaflets of the valve, but will rather engage with the fabric covering 120 over the stiffening element on the inflow aspect.

In an alternative embodiment of a spacer, a cover made of fabric or suitable material may be placed over the spacer itself or over a portion thereof. In a preferred embodiment, the spacer does not have a cover, since a cover can add expense to the spacer and/or increase a delivery profile thereof. Moreover, many transcatheter valves do not have a fabric cover, so a cover disposed over the spacer would have no benefit. On the other hand, as an alternative, a cover on the spacer device may encourage fibrous tissue overgrowth and incorporation of the spacer into the transcatheter valve and the surgical valve, and/or reduce perivalvular leakage around an implanted transcatheter valve.

Figure 12:
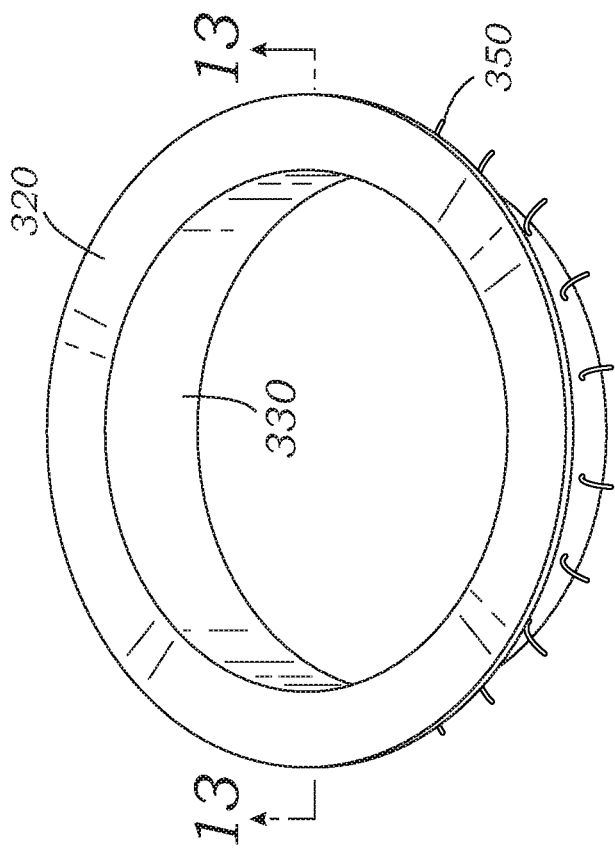
FIG. 12 illustrates an alternative embodiment in which the spacer has an upper flange and a spacer, but no downstream flange, with the struts not shown for simplicity.

FIG. 12 illustrates an alternative embodiment in which the spacer has an upstream flange 320 and a spacer shaft 330, but no downstream ring below the spacer 330. FIG. 13 is a cross-sectional view of the spacer of FIG. 12, both of which are shown without struts for simplicity of illustration, although the ring would normally have struts as in FIGS. 1 and 2. The spacer of FIG. 12 may be secured with anchors or spikes 350, for example, disposed on the lower or outflow surface of the upstream flange 320, and/or disposed on an outer wall of spacer shaft 330 as shown.

In an embodiment of the spacer ring that is balloon-expandable, the spacer is preferably made from a material that is fairly close in the galvanic series to the transcatheter valve and/or to the prosthetic surgical valve. In this way, there is not a stress corrosion problem between metal portions of the transcatheter valve, metal portions of the spacer, and/or metal portions of the prosthetic surgical valve, for example, the stent of the transcatheter valve contacting the spacer shaft, or the band of the prosthetic surgical valve contacting the anchors of the spacer. For example, the spacer ring may be made of one or more of a stainless steel alloy, titanium alloy, nitinol, or a cobalt-chromium alloy, depending on the material of the transcatheter valve. Cobalt-chromium has a similar oxidation potential to nitinol, and consequently cobalt-chromium is a preferred material for use with transcatheter valves that include nitinol frames. A cobalt-chromium spacer ring could then be used with a transcatheter valve including nitinol and/or cobalt-chromium, for example, in a stent or frame, to avoid a corrosion problem.

Spacer rings according to the present invention may be used to provide a dock that secures to an annuloplasty ring, such as the Carpentier-Edwards® Classic Annuloplasty Ring (Edwards Lifesciences, Irvine, Calif.) with a titanium core and fabric cover, or any of a wide variety of other annuloplasty rings. The annuloplasty ring reshapes the valve annulus, so that the native valve leaflets may properly coapt. Still, the native valve may ultimately need replacement with, for example, a transcatheter heart valve. A spacer structure that is secured to the annuloplasty ring may provide a docking region suitable for a THV to expand into and anchor. The drawings illustrate an exemplary D-shaped annuloplasty ring, although the spacer is applicable to rings of other shapes, including open rings or bands, as well as with rigid or flexible rings. Embodiments of the spacer are applicable to both mitral and tricuspid annuloplasty rings. In some embodiments, the spacer provides a structure at the open portion of an open ring that constrains THV expansion, for example, against the left ventricular tract (LVOT), thereby reducing the likelihood of LVOT obstruction in such cases. As with the embodiments of the spacer described and illustrated above, embodiments of annuloplasty-ring spacers have a longitudinal or vertical profile that permits the native leaflets to remain competent when the spacer is engaged to the annuloplasty ring, before a THV is deployed therein.

Figure 14:
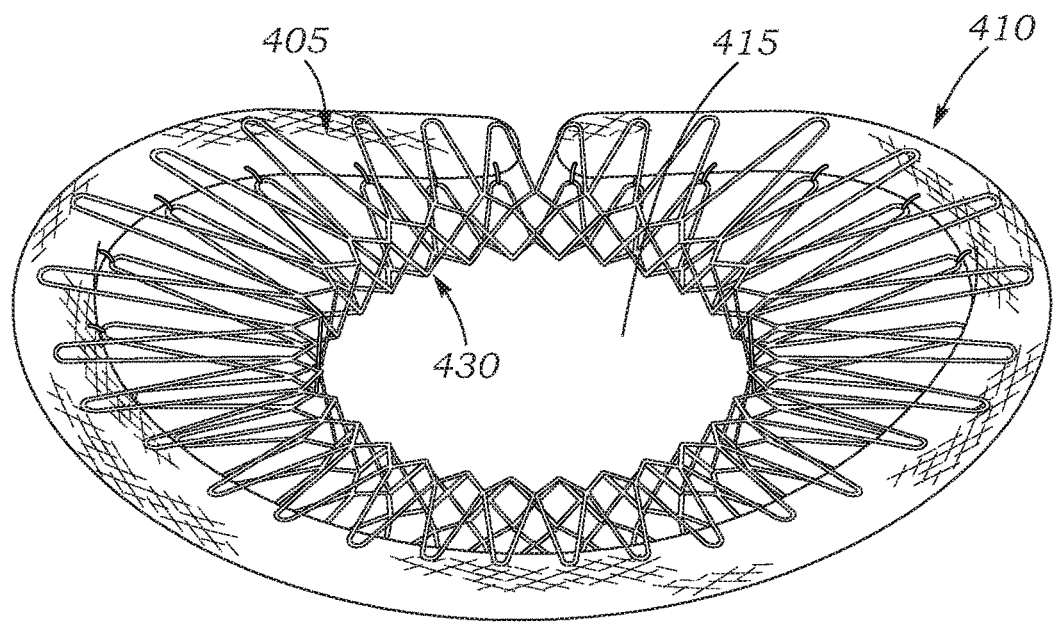
FIG. 14 is a perspective view of a spacer interconnected with an annuloplasty ring.
Figure 15:
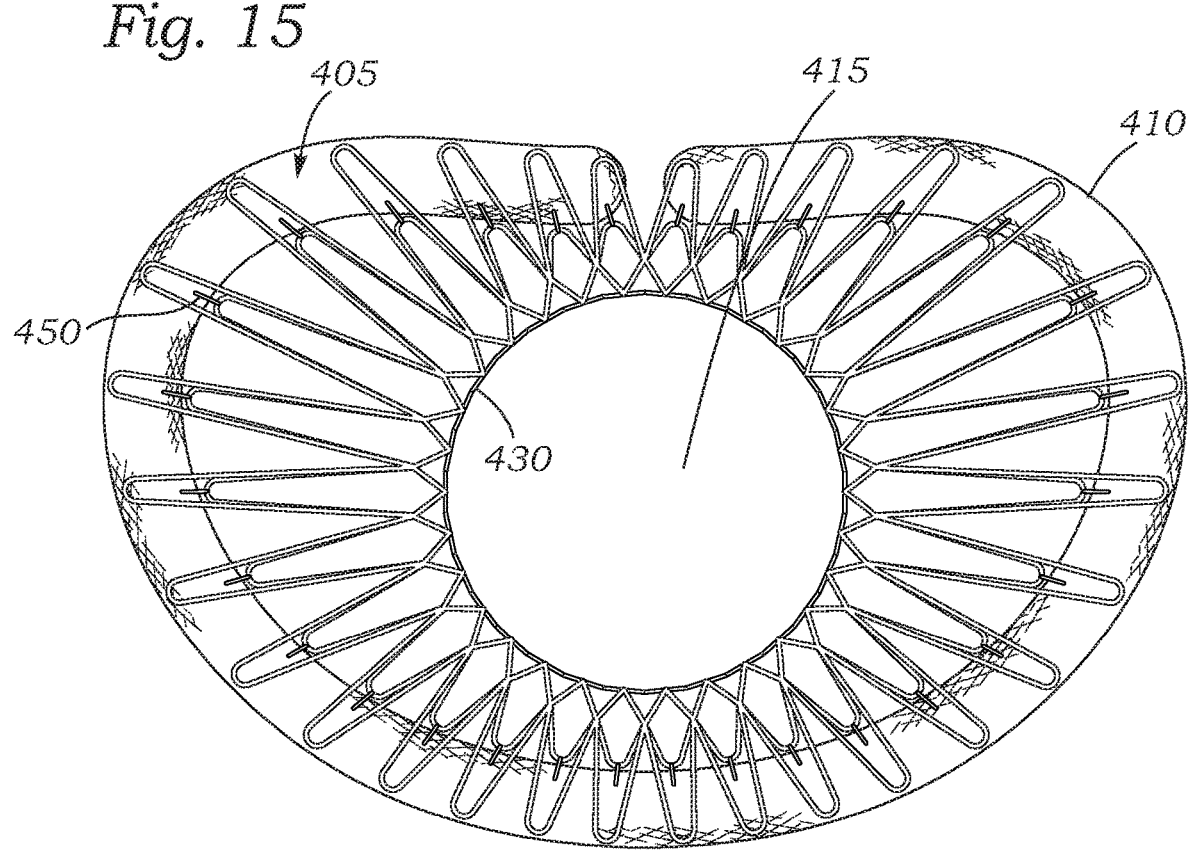
FIG. 15 is a top view of the annuloplasty ring of FIG. 14.
Figure 16:
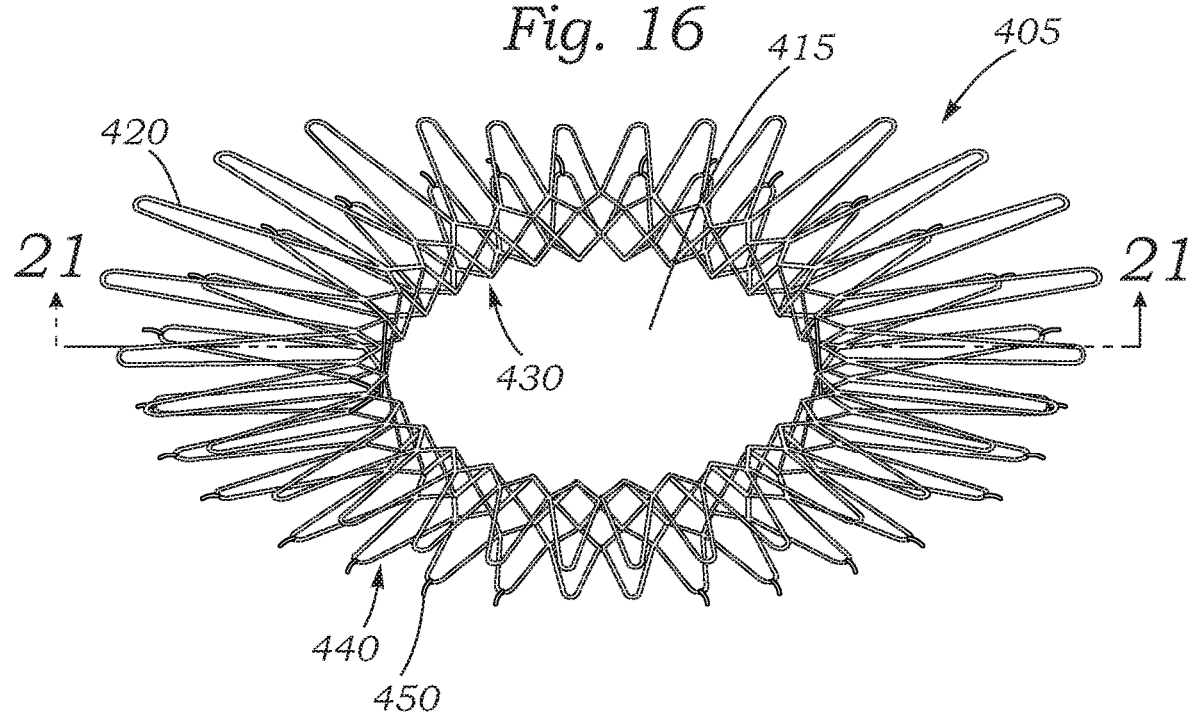
FIG. 16 is a perspective view of the spacer of FIGS. 14 and 15.
Figure 17:
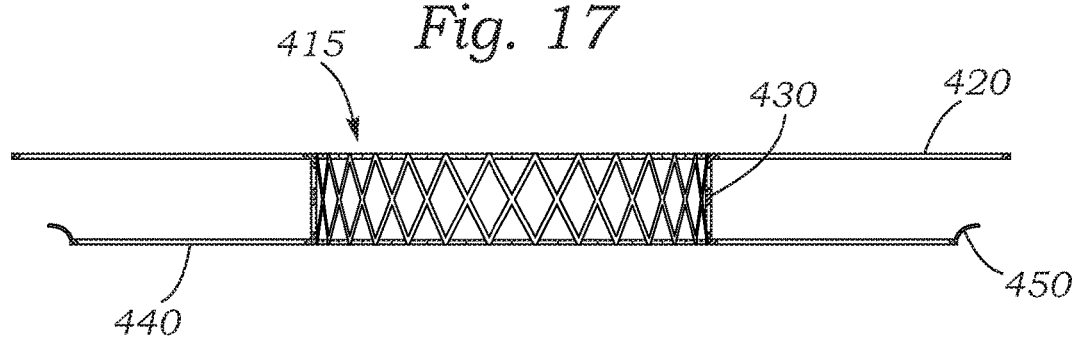
FIG. 17 is a cross-section of the spacer of FIG. 16 taken at line 17-17.
Figure 18:
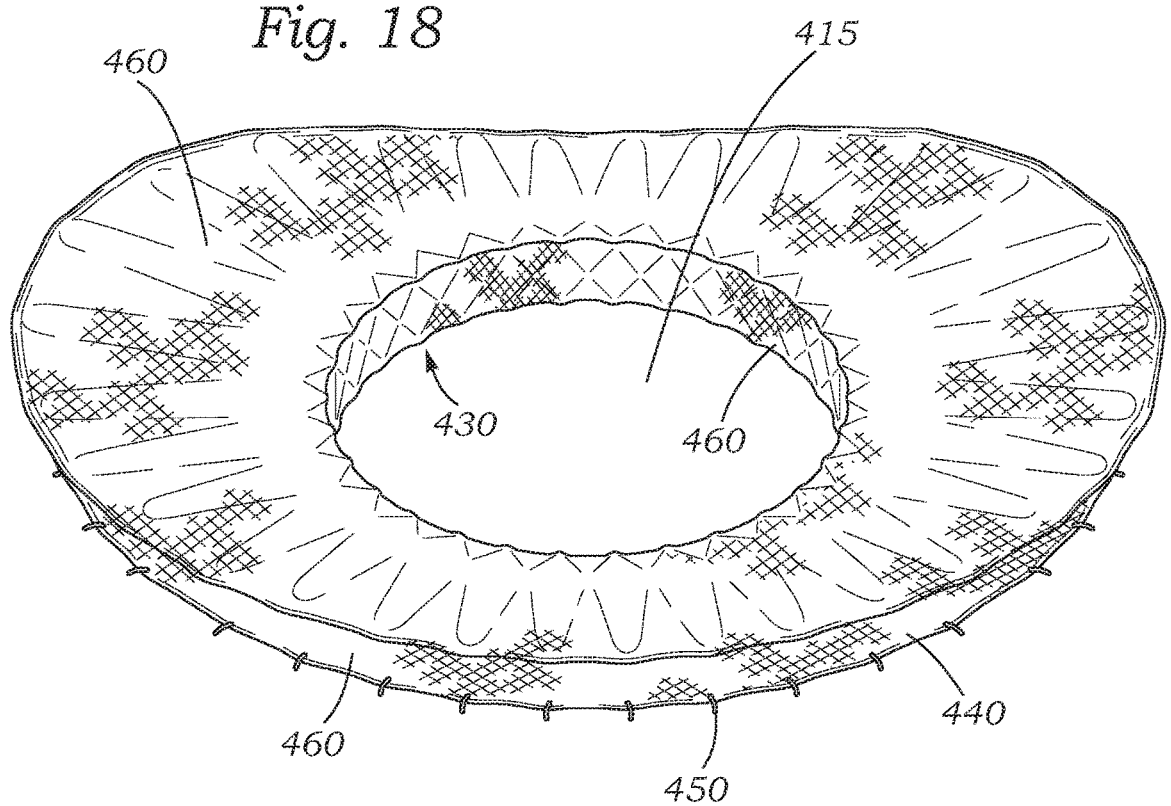
FIG. 18 is a perspective view of the spacer of FIG. 14 with a cover disposed thereover.
Figure 19:
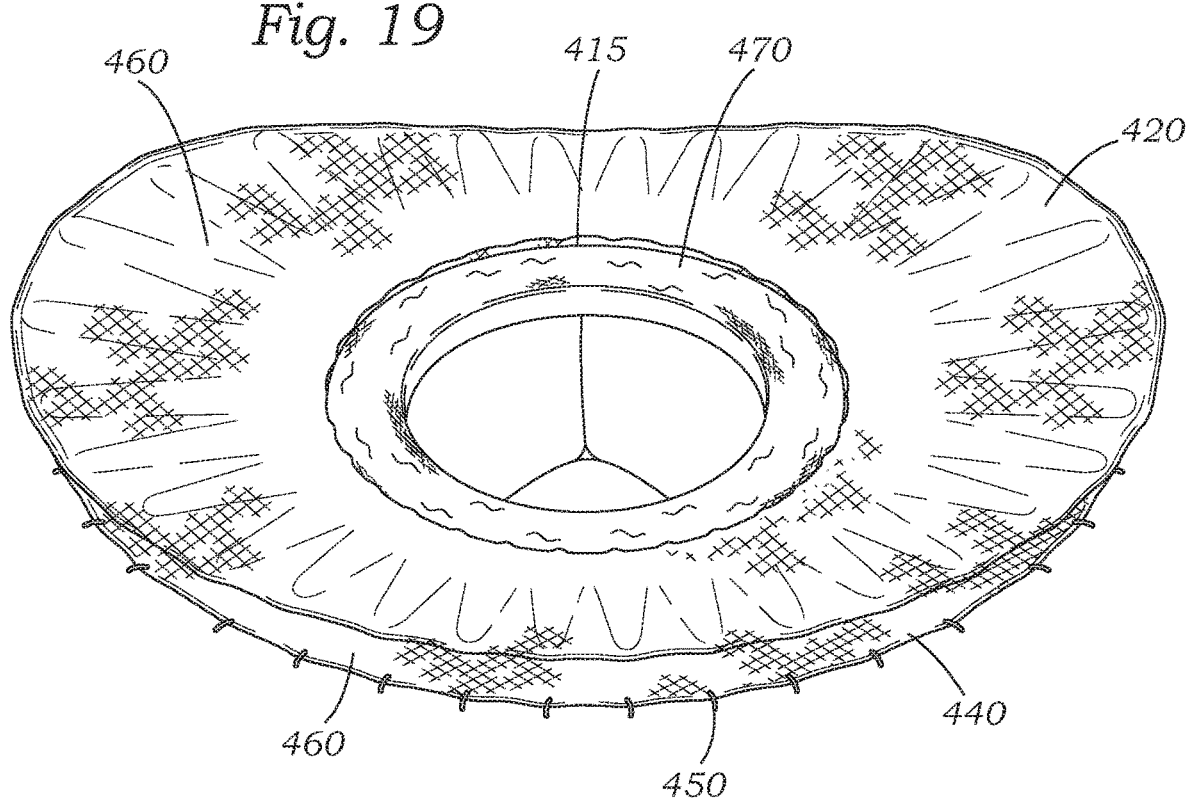
FIG. 19 illustrated the spacer of FIG. 18 with a transcatheter heart valve expanded therein.

FIGS. 14 and 15 illustrate a spacer 405 that is secured to a generally D-shaped annuloplasty ring 410. The spacer 405 includes a central open cylindrical shaft 415, an upper flange 420, a surface 430 within the cylindrical shaft onto which a THV can expand and anchor, and a lower flange 440. The curved armatures of the upper and lower flanges have lengths chosen to adapt to the shape of the annuloplasty ring 410. The annuloplasty ring 410 is typically covered with a fabric covering, and spikes 450 extend from the lower flange 440 into the fabric to help secure the spacer 405 to the annuloplasty ring 410. The upper flange 420 of the spacer is typically against an upper surface of the annuloplasty ring and may optionally secure to a fabric covering of the annuloplasty ring with spikes or other attaching means. FIGS. 16 and 17 illustrate the expanded spacer 405 in isolation.

The spacer may be secured to the annuloplasty ring in the manner illustrated in FIGS. 6-9. As with some other embodiments, snares may be used to control expansion of the spacer ring during deployment. Alternatively, the second flange may be deployed such that the annuloplasty ring is sandwiched in between the first and second flanges.

From another perspective, one embodiment of a docking station is designed to seal at the proximal inflow section to create a conduit for blood flow and to prevent pericardial leakage. The distal outflow section, however, is generally left open. In one specific embodiment, cloth, such as a polyethylene terephthalate (PET) cloth for example, or other material covers the proximal inflow section, but the covering does not cover at least a portion of the distal outflow section. The openings in the cloth are small enough to significantly impede blood passage therethrough. Again, a variety of other biocompatible covering materials may be used such as, for example, a fabric that is treated with a coating that is impermeable to blood, polyester, polytetrafluoroethylene fabric (PTFE, for example, ePTFE), a processed biological material, such as pericardium, or other coverings known in the art. The spacer ring may alternatively be fully covered, or covered only in selected areas. When the surface to which the THV secures is covered, the covering may assist in creating a tight seal and/or improving engagement with the THV.

In another aspect, the inner diameter of the spacer ring remains within the operating range of the THV. Consequently, the THV can operate within a space that otherwise would be too wide for the THV to operate properly, and/or in a space that otherwise would not permit a THV to reliably secure, for example, the D-shaped opening illustrated in the drawings.

As noted previously, the spacers may be self-expanding or balloon expanded. In a balloon expanded embodiment, one or more balloons inflates to expand the spacer. The balloons are removed, and a THV is delivered and expanded into the central shaft of the spacer. Other methods of expansion known in the art may be employed. For example, the spacer ring may be bundled with the THV prior to delivery, with both the spacer ring and the THV being delivered and expanded in a single delivery.

In another embodiment, the spacer may include a sensor, such as a pressure sensor. As one use for a sensor, the pressure of the docking station against the vessel wall may be detected during deployment. The sensor may communicate sensor data via a delivery catheter, for example. The data is used during balloon expansion, for instance, to determine when sufficient pressure against the vessel wall, the surgical valve and/or the annuloplasty ring as the case may be has been achieved, such that further expansion is not necessary. This approach may be useful when the dimensions, elasticity of the vessel walls, and/or other variables are uncertain prior to expansion of the docking station.

In another aspect, the outer surface of the spacer may be secured by positive pressure. A THV is expanded into the inner surface of the ring. The inner ring may be "spring loaded" to maintain force against the THV, thereby holding the THV in place. A stent structure in between the inner and outer ring surfaces may provide the spring loading. Alternatively, spring-like mechanisms may be built into the space in between the inner and outer ring surfaces.

In other alternative, an inner ring acts as a landing zone into which the THV docks. The inner ring may have a soft or compressible inner surface, such as foam, a resilient polymer, a hydrogel, or other suitable biocompatible material. The inner surface may give way under the force of the expanded THV. The area between the inner surface and outer surface of the ring may be sealed, such as with a fabric covering or a skirt that is on an interior surface of the ring, or otherwise have a surface that prevents the bypass of blood around the THV. It is noted that "ring" as used herein includes shapes that are not circular in cross-section, such as for example the outer ring that conforms to a D-shape or other shape in order to secure the outer ring to the supporting structure.

In view of the many possible embodiments to which the disclosed principles may be applied, it should be recognized that the illustrated embodiments are only preferred examples and should not be taken as limiting the scope of the disclosure. Rather, the scope is defined by the following claims. We therefore claim all that comes within the scope and spirit of these claims.

What is claimed is:

1. A method of securing a transcatheter heart valve within an annuloplasty ring that is D-shaped, the annuloplasty ring defining a D-shaped inner space and a central flow axis defining an upstream direction and a downstream direction, the downstream direction corresponding to the direction of blood flow from an upstream portion through a downstream portion of the annuloplasty ring, the method comprising steps of:

providing a collapsible spacer ring having an inner shaft adapted to receive the transcatheter heart valve, the spacer ring being oriented in the upstream and downstream directions when the spacer ring is implanted within the annuloplasty ring, the spacer ring having a D-shaped outer periphery when expanded while the inner shaft is cylindrical;

collapsing the spacer ring to a reduced diameter;

coupling the reduced diameter spacer ring to a distal end portion of an elongate catheter;

advancing the elongate catheter through a patient's vasculature and delivering the spacer ring into position within the D-shaped inner space of the annuloplasty ring;

expanding the spacer ring within the D-shaped inner space of the annuloplasty ring such that the D-shaped outer periphery conforms to the D-shaped inner space, the spacer ring inner shaft sized to provide a cylindrical engagement surface for securing the transcatheter heart valve therein; and expanding the transcatheter heart valve within the annuloplasty ring, the transcatheter heart valve securing to the engagement surface of the inner shaft of the spacer ring.

2. The method of claim 1, wherein the spacer ring is made of a metal that is close in the galvanic series to both a metal in the transcatheter heart valve and a metal in the annuloplasty ring.

3. The method of claim 1, wherein the spacer ring comprises anchors extending therefrom and the method includes, as the spacer ring is expanded, a step of securing the anchors into the inner space of the annuloplasty ring to maintain the spacer ring in position within the annuloplasty ring.

4. The method of claim 3, wherein the inner space of the annuloplasty ring is covered with a fabric, and the anchors secure into the fabric.

5. The method of claim 1, further comprising a step of controlling expansion of the spacer ring with snares coupled to the spacer ring.

6. The method of claim 1, wherein the step of expanding the spacer ring is accomplished with the spacer ring that is self-expandable.

7. The method of claim 1, wherein the step of expanding the spacer ring is at least partially accomplished with a balloon.

8. The method of claim 1, wherein the spacer ring is formed of expandable struts and has an expandable upstream flange and an expandable downstream flange, wherein the struts of the spacer ring have varying lengths chosen to form the D-shaped outer periphery.

9. The method of claim 1, wherein the spacer ring inner shaft is spring-loaded to provide an inward reaction force against the transcatheter heart valve.

10. The method of claim 1, wherein the spacer ring inner shaft is provided with a soft compressible docking inner surface selected from the group consisting of foam, a resilient polymer, a hydrogel, and a fabric covering.

11. The method of claim 1, wherein the step of expanding the spacer ring is at least partially accomplished with a balloon, wherein the spacer ring has a pressure sensor built-in and the method includes limiting an outward pressure exerted by the balloon.

12. A method of securing a transcatheter heart valve within a bioprosthetic heart valve with leaflets, the bioprosthetic heart valve having an inner space with an inside diameter and a central flow axis defining an upstream direction and a downstream direction, the downstream direction corresponding to the direction of blood flow from an upstream portion through a downstream portion of the bioprosthetic heart valve, the method comprising steps of:

providing a collapsible spacer ring having an inner shaft adapted to receive the transcatheter heart valve, the spacer ring being oriented in the upstream and downstream directions when the spacer ring is implanted within the bioprosthetic heart valve, the spacer ring having an expandable downstream spacer flange and an expandable upstream spacer flange;

collapsing the spacer ring to a reduced diameter;

coupling the reduced diameter spacer ring to a distal end portion of an elongate catheter;

advancing the elongate catheter through a patient's vasculature and delivering the spacer ring into position within the inner space of the bioprosthetic heart valve such that a downstream end of the spacer ring is positioned upstream from the leaflets of the bioprosthetic heart valve;

pushing at least the upstream spacer flange out of the catheter so that the upstream spacer flange expands, wherein an outside dimension of the upstream spacer flange is greater than the inside diameter of an upstream end of the inner space of the bioprosthetic heart valve;

displacing the catheter and the spacer ring in the downstream direction such that the upstream spacer flange contacts an upstream end surface of the bioprosthetic heart valve;

expanding the downstream spacer flange of the spacer ring within the inner space of the bioprosthetic heart valve with the downstream spacer flange positioned upstream from the leaflets of the bioprosthetic heart valve, the spacer ring inner shaft sized to provide an engagement surface for securing the transcatheter heart valve therein; and expanding the transcatheter heart valve within the bioprosthetic heart valve, the transcatheter heart valve securing to the engagement surface of the inner shaft of the spacer ring.

13. The method of claim 12, wherein the spacer ring is made of a metal that is close in the galvanic series to both a metal in the transcatheter heart valve and a metal in the bioprosthetic heart valve.

14. The method of claim 12, wherein the inner space of the bioprosthetic heart valve is covered with a fabric, and wherein the step of expanding the downstream spacer flange causes the downstream spacer flange to anchor into the fabric.

15. The method of claim 12, further comprising a step of controlling expansion of the spacer ring with snares coupled to the spacer ring.

16. The method of claim 12, wherein the spacer ring inner shaft is spring-loaded to provide an inward reaction force against the transcatheter heart valve.

17. The method of claim 12, wherein the spacer ring inner shaft is provided with a soft compressible docking inner surface selected from the group consisting of foam, a resilient polymer, a hydrogel, and a fabric covering.

18. The method of claim 12, wherein the step of expanding the spacer ring is at least partially accomplished with a balloon, wherein the spacer ring has a pressure sensor built-in and the method includes limiting an outward pressure exerted by the balloon.

19. The method of claim 12, wherein the upstream spacer flange has a radial dimension greater than the downstream spacer flange.

20. The method of claim 12, wherein the spacer ring is formed of self-expandable struts made of a shape memory material.

21. The method of claim 12, wherein the bioprosthetic heart valve has a stiffening band covered with fabric to partially define the inner space, and the downstream spacer flange expands and anchors to the fabric.

* * * * *